United States Patent [19]
McCarley et al.

[11] Patent Number: 5,794,625
[45] Date of Patent: Aug. 18, 1998

[54] MONITORING SYSTEM FOR ANIMALS

[75] Inventors: Stella A. McCarley, Rte. 1, Box 166-C, Dension, Tex. 75020; Steven J. Fisher, Bedford, Tex.

[73] Assignee: Stella A. McCarley, Denison, Tex.

[21] Appl. No.: 692,588

[22] Filed: Aug. 6, 1996

[51] Int. Cl.$^6$ ............................................. A61B 5/00
[52] U.S. Cl. ............................................. 128/736
[58] Field of Search ........................... 128/631, 736, 128/775, 903, 738

[56] References Cited

U.S. PATENT DOCUMENTS

| | | | |
|---|---|---|---|
| 4,028,687 | 6/1977 | Hamaguchi et al. | 128/775 |
| 4,630,613 | 12/1986 | Dennis | 128/775 X |
| 4,676,254 | 6/1987 | Frohn | 128/736 |
| 4,819,860 | 4/1989 | Hargrove et al. | 128/736 X |
| 4,854,328 | 8/1989 | Pollack | 128/736 |
| 4,981,139 | 1/1991 | Pfohl | 128/736 X |
| 4,994,665 | 2/1991 | Wernsing | 128/775 X |
| 5,033,864 | 7/1991 | Lasecki et al. | 128/736 X |
| 5,203,345 | 4/1993 | Kennedy et al. | 128/736 |

FOREIGN PATENT DOCUMENTS

| | | | |
|---|---|---|---|
| 986209 | 3/1976 | Canada | 128/775 |

*Primary Examiner*—Francis Jaworski
*Attorney, Agent, or Firm*—Jerry C. Ray

[57] ABSTRACT

An animal monitoring system includes a temperature monitoring unit which is governed by a microcontroller, i.e., an electronic computer, and which is placed inside an animal's body, usually inside the birth canal. An inactive or sleep mode of the monitoring unit reduces battery drain. Periodically the monitoring unit enters an active mode during which a temperature of the surroundings is measured; the analog temperature is converted to digital data, then transmitted as an UHF, low-power radio signal via a self-contained antenna. A base unit receives the signal, displays the received temperature value, compares the received temperature value to a predetermined range of temperature values, and initiates an alarm condition if the received temperature is outside the predetermined range. The alarm condition also results if the animal strays and the signal is lost. The alarm condition includes an audible and/or visual alarm, either at the base unit or at a remote location, and may include dialing preselected telephone numbers and transmitting a prerecorded message when such an automatically dialed call is answered.

6 Claims, 3 Drawing Sheets

MONITORING SYSTEM FOR ANIMALS

BACKGROUND OF THE INVENTION

1. Field of the Invention

This invention relates to systems for monitoring animals by low-power radio signals, and particularly to such systems providing an animal temperature sensor connected to a radio-frequency transmitter and a base station providing temperature read-out and means for signaling an alarm condition.

2. Description of the Related Art

Animals have value to their owners for a variety of reasons, including sentimental attachments as well as monetary or market value. Monitoring the location and condition of animals is desirable any time an animal is subjected to stressful conditions; this is especially true when expensive animals such as thoroughbred horses are giving birth. Because both the mare and her foal are potentially at risk, it is desirable to have a monitoring system which will alert the owner or trainer if the animal strays or begins labor. The monitor should be effective and simple in operation, and capable of being installed by non-skilled persons, i.e., not requiring the assistance of a veterinarian for installation. It is further desirable to have such a system which will monitor the general location of an animal, in addition to providing an early warning of the onset of parturition.

Several attempts have been made to solve the problems described above. Hamaguchi (U.S. Pat. No. 4,028,687) discloses an egg-shaped capsule surrounded by a skirt or flange which is inserted into the birth canal of an animal prior to the expected delivery date; the device has an external antenna for transmitting a signal. Zartman (U.S. Pat. No. 4,651,437) discloses an internal temperature sensor contained within a housing having an expandable framework for retaining the housing within the birth canal. Harvey (U.S. Pat. No. 3,583,389) discloses an egg-shaped container containing a temperature sensor; the device transmits a signal on detecting a change in temperature when it is expelled by labor contractions. Wernsing (U.S. Pat. No. 4,994,665) has a similar device which relies on the detection of light after being expelled from the animal's birth canal.

SUMMARY OF THE INVENTION:

Body temperature of an animal such as a horse is monitored by a temperature sensor placed in the birth canal of the animal. The sensor provides very accurate monitoring of internal body temperature; readings are taken at intervals. Between active periods, the monitor circuitry and associated transmitter circuitry are in a sleep mode to reduce battery drain. Low-power radio signals are transmitted via an antenna contained within the temperature-monitoring capsule; the signals are received by a base station having an associated read-out to display temperature readings of a particular animal. If an animal strays so that the radio signals are lost, the base unit activates its alarm mode. Onset of parturition causes the expulsion of the transmitter unit from the birth canal; the difference in outside temperature versus animal body temperature is recognized by the base unit as being outside preset parameters, and an alarm is sent.

Based on the above, it is an object of this invention to provide an apparatus and method for monitoring body temperature in animals and humans.

A further object is to provide a temperature-monitoring system which is used to provide warning of the onset of parturition in animals, both feral and domestic.

Another object is to provide a detector for the onset of parturition which has improved means for retention inside a birth canal.

Another object is to provide a parturition detector which will activate a remote alarm system, including dialing pre-programmed telephone numbers.

Further objects are to provide a temperature monitor system which is compact, durable, lightweight, safe, and reliable, yet inexpensive and easy to install and operate.

The specific nature of the invention, as well as other objects, uses, and advantages thereof, will clearly appear from the following description and from the accompanying drawings, the different views of which are not necessarily scale drawings.

Figure 1:
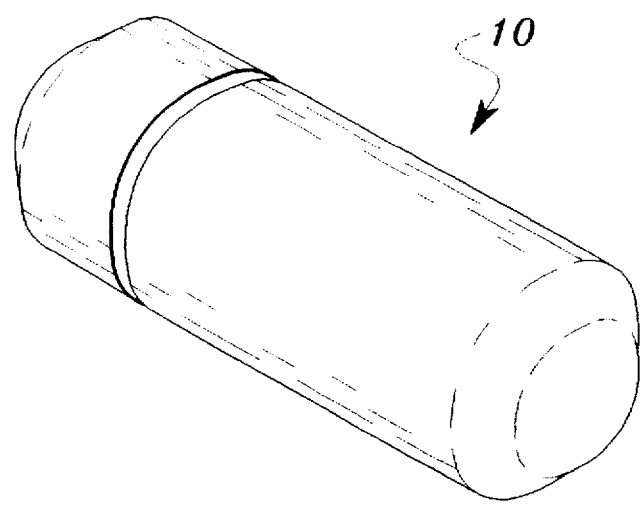
FIG. 1 shows the watertight case for the transmitter unit.

CATALOG OF THE ELEMENTS:

To aid in the correlation of the elements of the invention to the exemplary drawings, the following catalog of the elements is provided:
10 transmitter unit
12 transmitter unit case
14 transmitter unit cap
16 spring
18 battery
20 circuit board

Figure 2:
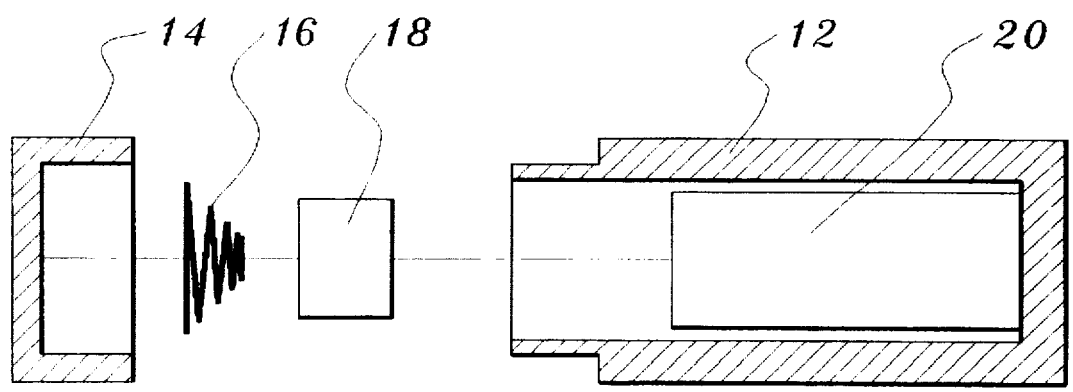
FIG. 2 is an exploded view of the transmitter unit.

DESCRIPTION OF THE PREFERRED EMBODIMENTS:

This description is largely in terms of applications of the invention to horses, but it is understood that the invention may be applied to other animals, including male animals. Referring to the drawings, FIG. 1 shows a transmitter unit 10 which is placed inside a mare's birth canal. Housed in a watertight cylindrical case, the transmitter unit includes a temperature sensor, battery, FM radio transmitter, and associated control circuitry. FIG. 2 is a schematic of the transmitter unit 10, showing case 12, and cover or cap 14 which screws onto case 12 to make a watertight container. Contact maintenance spring 16 presses battery 18 against electrical contacts; circuit board 20 contains the components described below.

Figure 3:
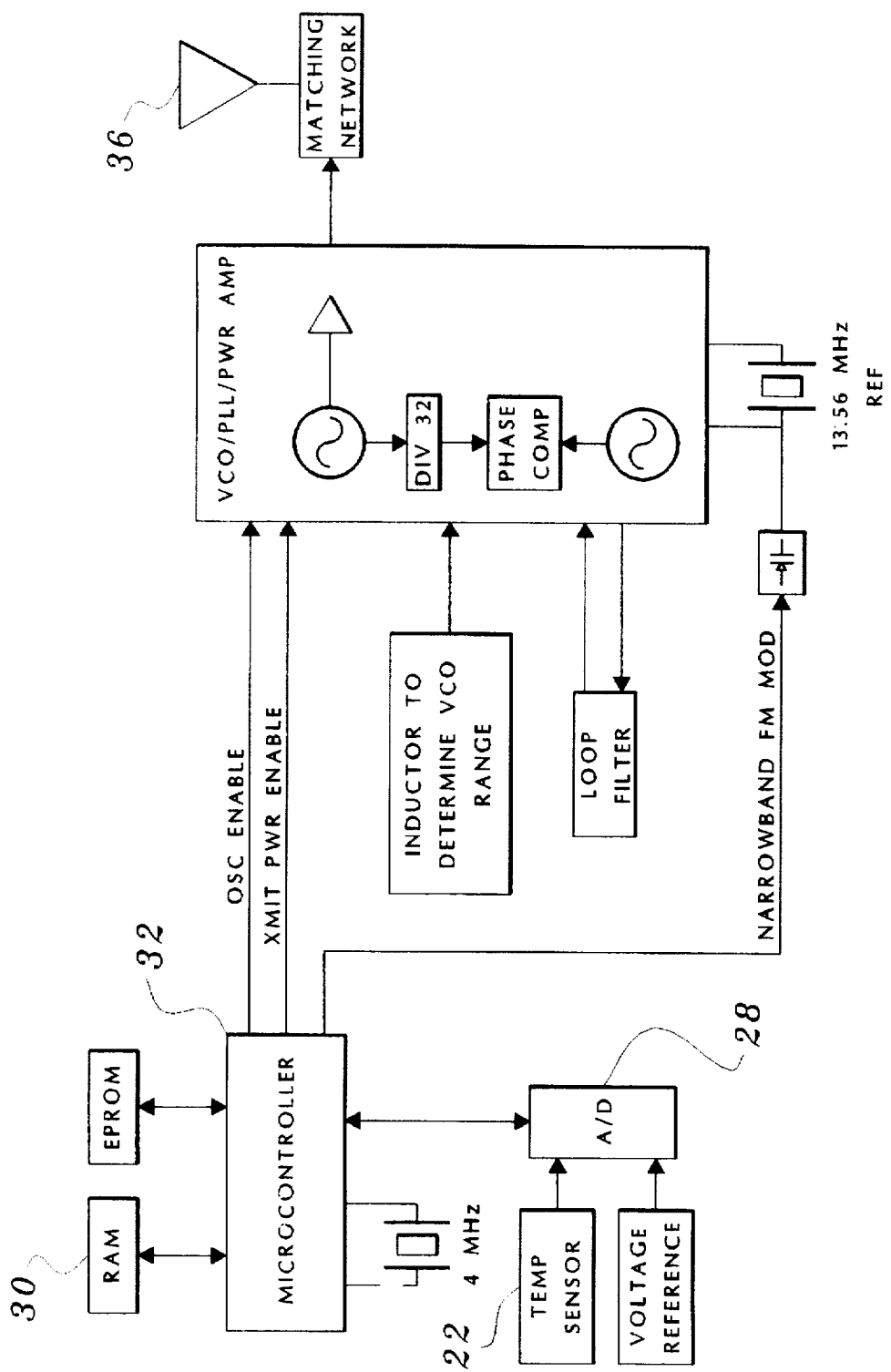
FIG. 3 is a block diagram of the transmitter unit circuitry.
Figure 4:
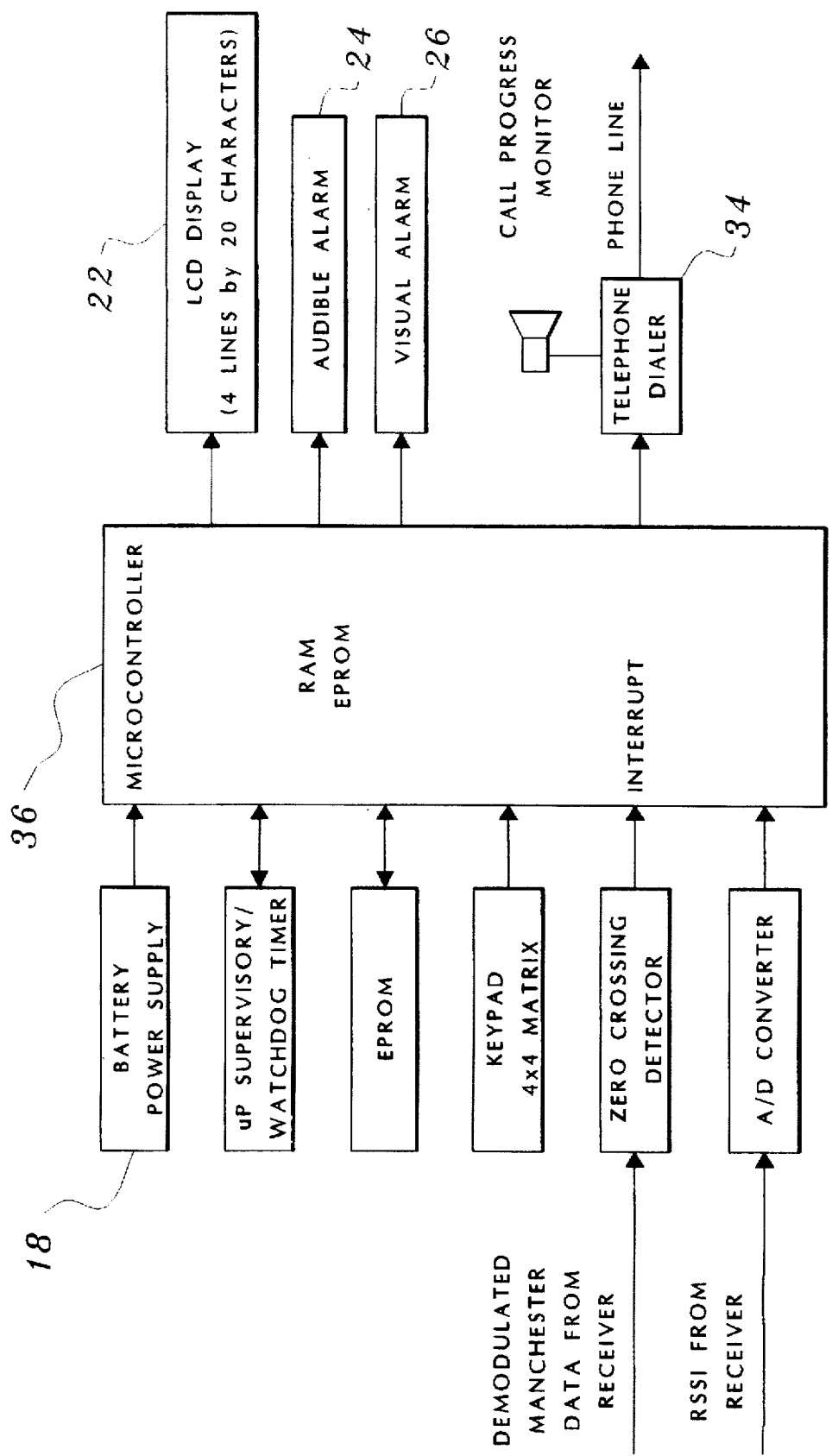
FIG. 4 is a block diagram of the base station circuitry.

FIG. 3 is a block diagram of the major components of the transmitter unit. FIG. 4 is a block diagram of the base station, which monitors the frequency used by the transmitters as described below. Up to 10 transmitter units can be monitored by the base station.

A horse's normal body temperature is about 99° F. Referring now to FIG. 3, a voltage proportional to the horse's temperature is generated by the temperature sensor in the transmitter unit. An example of a suitable sensor is the National Semiconductor LM334; this unit generates 3.05 mV per degree F above 0° K, having an output of about 1.7 V at 99° F. A voltage reference provides a standard voltage output; varying output from the temperature sensor is compared to the voltage reference.

Output from the temperature sensor is converted from analog to digital in a converter which has a power-down mode, allowing the transmitter unit to go into a "sleep mode" during which battery drain is reduced. As described below, the length of the cycle is responsive to the value of the monitored animal's temperature. Value, as used herein, means a numerical quantity determined by calculation or by measurement. The digital converter used in the prototype of the present invention is a Linear Technology LTC1285 Analog/Digital converter. This model is capable of transmitting twelve bits of temperature data; a calibration offset is applied to the data prior to transmission, however, reducing the temperature data to eight bits for transmission.

When in the sleep mode mentioned above, the only part of the circuitry in operation is a timer circuit connected to the microcontroller. Containing RAM and EPROM memory as shown in FIG. 5, the microcontroller governs all the functions of the transmitter unit. The timer circuit sends an activate signal to the microcontroller approximately every 15 seconds. The activate signal causes the microcontroller to initiate a temperature measurement. The measured temperature will be transmitted to the base station if any of the following conditions are met:

1. The measured temperature is outside the range of 94°–104° F.
2. The measured temperature has changed 1.0° or more from the previously transmitted reading.
3. More than approximately 2 minutes have elapsed since the last transmission.

Any of the parameters described above, which are contained within the software, may be changed by reprogramming. After the timer circuit has activated the microcontroller, the microcontroller causes power to be applied to the temperature sensor described above. After a delay for the temperature measurement to stabilize, the analog-to-digital converter converts the analog output of the temperature sensor to digital data, which is stored in RAM.

An identification number for each transmitter unit is stored in the EEPROM of that unit; the identification number is transmitted with the temperature value during each active cycle. A checksum is calculated by the controller for transmission with the data packet containing the temperature value. The value of the checksum is a function of the transmitter unit identification number and the recorded temperature value; the checksum changes as the recorded temperature changes. The base unit (described below) recalculates the checksum when it receives a data packet from a transmitter unit. If the checksum calculated by the base station does not match that sent by the transmitter unit, that particular data packet is discarded. A series of non-matching checksums initiates an alarm condition at the base station.

The transmitter portion of the transmitter unit is a narrowband FM transmitter operating in the 420–470 MHz UHF band, which sends its signal via a self-contained antenna. A data packet containing a synchronization signal, unit identification number, temperature value, and checksum is transmitted at the end of each active cycle. Transmission of the packet requires less than 10 mS; when the transmission is complete the microcontroller reverts back to the power-down or sleep mode.

The transmitter is low-power, generating a signal strength of just below 4400μV per meter at a distance of three meters, to remain below the maximum allowable signal strength for its frequency band, per 47 C.F.R. 15.231(e).

The second major component of the invention is a base unit which receives on a narrowband FM receiver the data packet sent by the transmitter unit. Referring now to FIG. 4, a microcontroller inside the base unit decodes the data containing the temperature value. On receiving the transmitted signal, the base station displays the temperature value directly on an LCD readout on the base unit. In addition, the temperature value is compared with a range of preselected temperature values contained in the EPROM of the microcomputer. Where the received temperature value falls outside the preselected range of temperatures, an alarm condition is triggered. The range of temperature values contained in the base unit memory which trigger an alarm may be different from the range of values contained in the memory of the remote transmitter, described previously, which cause the transmission of a temperature. Visual and/or audible alarms may be provided at the location of the base unit, which typically would be in a stable, or at a remote location such as a residence.

Another method of sending the alarm signal is via telephone. An automatic dialer within the base unit selects from a list of telephone numbers and dials them in sequence. After a predetermined delay time after dialing, the base unit transmits its message. The delay time, which is programmable by a user of the system, is variable to accommodate different paging services which answer a call after different numbers of rings. Of course, this provision requires the connection of either a telephone line or a cellular telephone to the base unit.

Because the FM signal transmitted by the monitoring unit is very low power, reception by the base unit is sensitive to the distance between monitoring unit and base unit. If the distance is more than about 600 feet, the signal strength of the remote monitoring unit will be too weak for the base unit to receive, and the base unit triggers a "loss-of-signal" condition. The lost-signal mode is the same as the alarm mode described above, except that both visual alarm indications and the automatic telephone message are different. Difference in the types of signals allows the owner or trainer to quickly determine what type of situation to expect. Other factors such as the size and location of the receiving antenna, and obstructions such as metal buildings also affect the effective transmission range.

As shown in FIG. 4, the base unit includes a keypad for reprogramming by a user, an LCD readout for display of temperature readings and other data, and an autodialer for telephones as described above.

The restrictive description and drawings of the specific examples above do not point out what an infringement of this patent would be, but are to enable one skilled in the art to make and use the invention. Various modifications can be made in the construction, material, arrangement, and operation, and still be within the scope of my invention. The limits of the invention and the bounds of the patent protection are measured by and defined in the following claims.

We claim as our invention:

1. An apparatus for monitoring body temperature of an animal, comprising:

a) a monitoring unit having means for sensing a body temperature of the animal and means for electronically transmitting said body temperature.

b) said monitoring unit adapted to be placed within a birth canal of the animal being monitored, c) said monitoring unit alternating between an active mode and an inactive mode, d) said monitoring unit responding to the onset of parturition by detecting a temperature change when said device is expelled from the birth canal of the animal being monitored and by transmitting a signal responsive to said temperature change.

e) a base unit for receiving electronically transmitted body temperature from at least said one monitoring unit, f) said base unit including means for displaying said body temperature, g) said base unit including means for comparing said body temperature transmitted by said monitoring unit with a preselected range of temperatures, and h) means for generating an alarm when said body temperature is outside said preselected range of temperatures.

2. The invention as described in claim 1, wherein:

g) said monitoring unit includes a temperature sensor for generating a voltage proportional to the animal's temperature, h) an analog-to-digital convertor connected to an output of said temperature sensor, i) memory for storing temperature data from said convertor and for storing a monitoring unit identification number, j) a low-power radio transmitter for sending temperature data to a base unit, k) a microcontroller to activate components of said monitoring unit in a predetermined sequence, and l) a battery to supply electrical power to components of said monitoring unit.

3. The invention as described in claim 1, wherein said means for generating an alarm includes an audible alarm and a visual alarm.

4. The invention as described in claim 1, wherein said means for generating an alarm includes means for automatically dialing at least one telephone number and transmitting via telephone a predetermined signal.

5. A method of monitoring the body temperature of an animal comprising the steps of:

a) placing a temperature monitoring device inside an animal's body, said device alternating between an active mode and an inactive mode, b) monitoring with said device a temperature of the animal, c) transmitting periodically a temperature value from said temperature monitoring device to a base unit, d) displaying said temperature values, e) comparing said temperature values to a preselected range of temperatures, f) generating an alarm when said temperature is outside said preselected range of temperatures, including dialing from said base unit at least one preselected telephone number, and h) transmitting a prerecorded message after a telephone call is answered.

6. The method as described in claim 5, wherein the step of generating an alarm further comprises:

i) generating an alarm responsive to loss of a signal from said temperature monitoring device.

* * * * *